US00PP16525P2

(12) United States Plant Patent
Trees

(10) Patent No.: US PP16,525 P2
(45) Date of Patent: May 9, 2006

(54) ***VERBENA* PLANT NAMED 'BALAZMAPURP'**

(50) Latin Name: *Verbena hybrida*
Varietal Denomination: Balazmapurp

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 61 days.

(21) Appl. No.: 11/017,547

(22) Filed: Dec. 20, 2004

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Verbena* plant named 'Balazmapurp' characterized by its purple-colored flowers, intermediate serrate, dark green-colored foliage, good basal branching character, and spreading and trailing growth habit.

1 Drawing Sheet

Figure 1:
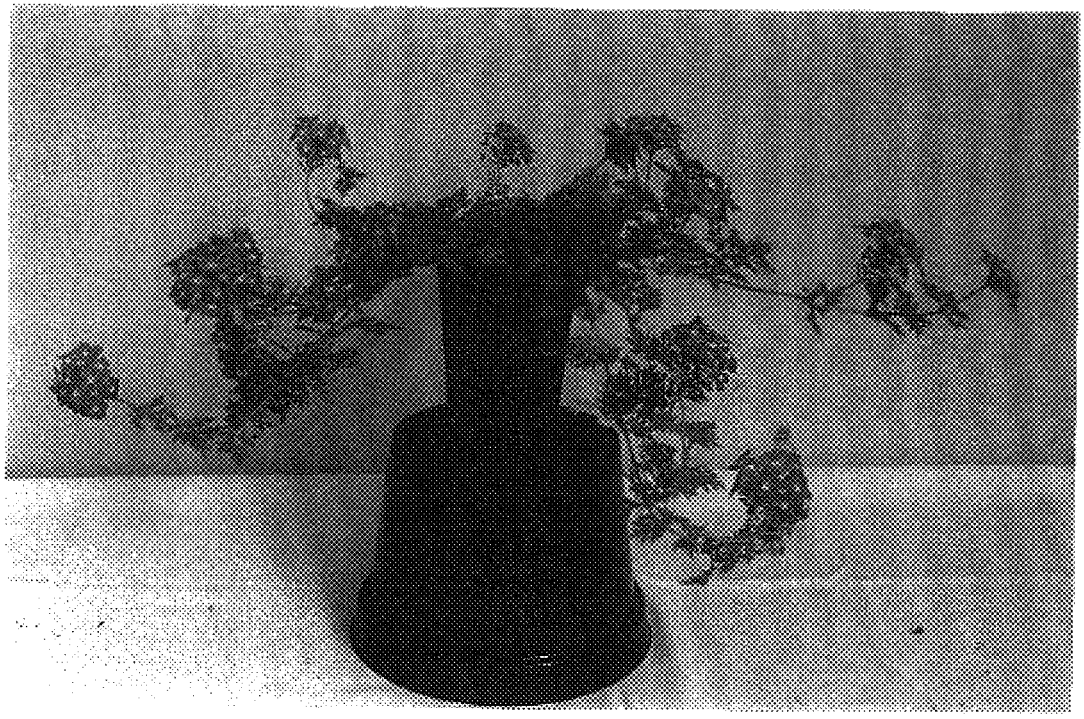
Figure 2:
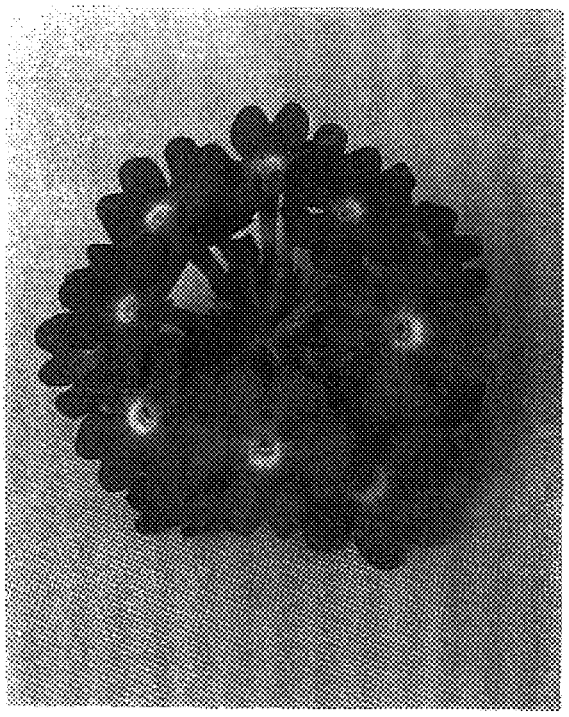

Latin name of genus and species of plant claimed: *Verbena hybrida.*
Variety denomination: 'Balazmapurp'.

BACKGROUND OF THE INVENTION

The present invention comprises a new and distinct *Verbena* plant, botanically known as *Verbena hybrida,* and hereinafter referred to by the cultivar name 'Balazmapurp'.

The new cultivar was developed by the inventor through a controlled breeding program during December 2001 at Arroyo Grande, Calif. The objective of the breeding program was the development of *Verbena* cultivars with a trailing habit, continuous flowering, excellent basal branching, small, dark green-colored foliage, and attractive flower coloration.

The female (seed) parent of the new cultivar was the *Verbena hybrida* cultivar Balazdapi, U.S. Plant Pat. No. 12,807, which exhibits a mounded-trailing growth habit, dark purple-colored flowers, and dark green-colored foliage. The male (pollen) parent of the new cultivar was the *Verbena tenuisecta* cultivar Serenity Lavender, not patented, which exhibits a mounded-trailing growth habit, light lavender-colored flowers, and small, serrated dark green-colored leaves.

The new cultivar was discovered and selected by the inventor as a single flowering plant within the progeny of the above cross-pollination in April 2002. Asexual reproduction of the new cultivar by terminal stem cuttings in West Chicago, Ill. since April 2002 has demonstrated that the characteristics of the new cultivar, as herein described, reproduce true to type and are firmly fixed and retained through successive generations of such asexual propagation.

SUMMARY OF THE INVENTION

The following characteristics of the new cultivar been repeatedly observed and can be used to distinguish 'Balazmapurp' as a new and distinct cultivar of *Verbena* plant:

1. Purple-colored flowers.
2. Intermediate serrate, dark green-colored foliage.

3. Good basal branching character.
4. Spreading and trailing growth habit.

Plants of the new cultivar differ from the female parent primarily in flower color and leaf margin and from the male parent primarily in flower color and leaf margin.

Plants of the new cultivar are most similar to the cultivar Lanai™ 'Blue', not patented. However, in side-by-side comparison, plants of the new cultivar differ from plants of Lanai™ 'Blue' by the following characteristics:

1. Plants of the new cultivar have smaller flowers than plants of Lanai™ 'Blue'.
2. Plants of the new cultivar are more floriferous than plants of Lanai™ 'Blue'.
3. Plants of the new cultivar are narrower than plants of Lanai™ 'Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from color values sited in the detailed description, which more accurately describes the colors of 'Balazmapurp'. The plants were grown in 10 cm pots for 12 weeks in a greenhouse at West Chicago, Ill.

FIG. 1 illustrates a side view of the overall growth and flowering habit of 'Balazmapurp'.

FIG. 1 illustrates a close-up view of an individual inflorescence of 'Balazmapurp'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004. The readings were taken between 11:00 and 11:30 a.m. under natural light conditions.

The following descriptions and measurements describe plants produced from cuttings taken from stock plants and grown in a double polycarbonate-covered greenhouse under conditions comparable to those used in commercial practice. Plants were grown at West Chicago, Ill. in 10 cm pots for 12 weeks utilizing a soilless growth medium. Greenhouse temperatures were maintained at approximately 70–80° F. (21–26° C.) during the day and approximately 62–65° F. (17–18° C.) during the night. Greenhouse light levels were maintained at approximately 5,000–8,000 footcandles during the day.

Botanical classification: *Verbena hybrida* cultivar 'Balazmapurp'.

Parentage:

*Female parent.*—'Balazdapi', U.S. Plant Pat. No. 12,807.

*Male parent.*—'Serenity Lavender', not patented.

Propagation:

*Type cutting.*—Terminal tip.

*Time to initiate roots.*—Approximately 6–9 days.

*Time to produce a rooted cutting.*—Approximately 21–28 days.

*Root description.*—Fibrous.

*Rooting habit.*—Freely branching.

Plant description:

*Crop time.*—Approximately 5–7 weeks from a rooted cutting.

*Growth habit.*—Moderately vigorous with good basal branching. Pinching improves basal branching.

*Form.*—Spreading and trailing.

*Size.*—Height from soil level to top of plant plane: Approximately 9.4 cm. Width (area of spread): Approximately 53.6 cm.

*Branch.*—Quantity: Approximately 6 per plant. Shape: Square in cross section. Length: Approximately 21.5 cm. Diameter: Approximately 1.6 mm. Texture: Densely pubescent. Color: 144B. Length of internode at middle of branch length: Approximately 2.5 cm.

*Foliage.*—Type: Simple. Fragrance: None. Arrangement: Opposite. Orientation to stem: Right angle. Shape: Ovate. Margin: Parted. Apex: Acute. Base: Attenuate. Texture of upper surface: Densely covered with short stiff hairs. Texture of lower surface: Glabrous except for dense pubescence along veins. Leaf length: Approximately 2.1 cm. Leaf width: Approximately 2.2 cm at widest point. Color of upper surface of mature leaf: Closest to 137B with venation of 145B. Color of lower surface of mature leaf: Darker than 138A, with venation of 145B. Petiole length: Approximately 6.2 mm. Petiole diameter: Approximately 2 mm. Petiole texture: Pubescent on lower surface and along margin and glabrous on upper surface. Petiole color: 145B.

Flowering description:

*Flowering habit.*—'Balazmapurp' is freely flowering under outdoor growing conditions with substantially continuous flowering from spring through autumn and year round in greenhouse environment.

*Inflorescence.*—Type: Corymb. Quantity per plant: Approximately 9. Height: Approximately 3.6 cm. Width: Approximately 4.5 cm. Quantity of fully opened flowers per inflorescence at any one time: Approximately 24 cm.

*Peduncle.*—Length: Approximately 4.2 cm. Diameter: Approximately 2.2 mm: Texture: Densely pubescent. Color: 144A.

*Lastingness of bloom.*—Approximately 5–7 Days.

Flower description:

*Bud.*—Rate of opening: Generally takes 3–6 days for bud to progress from first color to fully open floret. Shape: Spherical to oval. Length: Approximately 2.6 mm. Diameter: Approximately 2.6 mm. Color: N88B.

*Type.*—Salverform. Corolla shape: Round. Corolla diameter: Approximately 1.6 cm.

*Petals.*—Quantity: Five, fused at base forming tube. Shape: Obovate. Appearance: Velvety. Margin: Entire. Apex: Emarginate. Texture of upper surface: Glabrous. Texture of lower surface: Puberulent. Color of upper surface when first open: N81A. Color of upper surface when fully open: Between N82A and N87A. Color of lower surface: N87B. Whiskers of 155C surround the opening of the corolla tube. Petal color at sensecence: 95A.

*Corolla tube.*—Length: Approximately 1.6 cm. Diameter at apex: Approximately 2.0 mm. Diameter at base: 1.0 mm. Texture of inner surface: Pubescent. Texture of outer surface: Puberulent. Color of both inner and outer surfaces: 155C.

*Calyx.*—Shape: Tubular, formed by 5 fused sepals, 5 toothed, 5 ribbed, with stipule. Length: Approximately 8.8 mm. Diameter at apex: Approximately 2 mm. Diameter at base: Approximately 2 mm. Color of inside/upper-surface: 143D. Color of outer/lower-surface: 143D. Stipule shape: Lanceolate. Stipule apex: Acute. Stipule base: Truncate. Stipule Margin: Entire. Stipule length: 4 mm. Stipule width at base: 2 mm. Stipule texture: Upper surface: Glabrous. Lower surface: Pubescent. Stipule color: 143B.

*Reproductive organs.*—There are 4 stamens. Anther shape: Bi-lobed. Anther length: 0.6 mm. Amount of pollen: None observed. Pistil quantity: 1 per flower. Pistil length: 1.38 cm. Stigma shape: Funnel. Stigma length: 1.2 mm. Stigma color: 145A. Style length: Approximately 1.1 cm. Style color: 145B. Ovary diameter: 1.6 mm. Ovary color: N144C.

Seed and fruit production: Neither seed nor fruit production has been observed.

Disease and pest resistance: Resistance to pests and pathogens common to *Verbena* has not been observed.

What is claimed is:

1. A new and distinct cultivar of *Verbena hybrida* plant named 'Balazmapurp', substantially as herein shown and described.

* * * * *